(12) United States Patent
Liu et al.

(10) Patent No.: US 12,404,528 B2
(45) Date of Patent: Sep. 2, 2025

(54) RECOMBINANT STRAIN FOR PRODUCING SHIKIMIC ACID, AND CONSTRUCTION METHOD AND USE THEREOF

(71) Applicant: JIANGNAN UNIVERSITY, Wuxi (CN)

(72) Inventors: Liming Liu, Wuxi (CN); Qiang Ding, Wuxi (CN); Xiulai Chen, Wuxi (CN); Cong Gao, Wuxi (CN); Liang Guo, Wuxi (CN); Guipeng Hu, Wuxi (CN); Jia Liu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 476 days.

(21) Appl. No.: 17/693,349

(22) Filed: Mar. 12, 2022

(65) Prior Publication Data

US 2023/0332190 A1    Oct. 19, 2023

Related U.S. Application Data

(63) Continuation-in-part of application No. PCT/CN2021/135282, filed on Dec. 3, 2021.

(30) Foreign Application Priority Data

Nov. 26, 2021 (CN) .......................... 202111425348.1

(51) Int. Cl.
| | |
|---|---|
| C12P 7/42 | (2006.01) |
| C12N 1/21 | (2006.01) |
| C12N 9/10 | (2006.01) |
| C12N 9/12 | (2006.01) |
| C12N 9/88 | (2006.01) |
| C12N 15/70 | (2006.01) |
| C12R 1/19 | (2006.01) |

(52) U.S. Cl.
CPC .............. *C12P 7/42* (2013.01); *C12N 9/1022* (2013.01); *C12N 9/1085* (2013.01); *C12N 9/1205* (2013.01); *C12N 9/88* (2013.01); *C12N 15/70* (2013.01); *C12R 2001/19* (2021.05); *C12Y 202/01001* (2013.01); *C12Y 205/01054* (2013.01); *C12Y 207/01071* (2013.01); *C12Y 402/03004* (2013.01)

(58) Field of Classification Search
None
See application file for complete search history.

(56) References Cited

U.S. PATENT DOCUMENTS

2019/0322980 A1* 10/2019 Bowman ................ C12N 15/86

FOREIGN PATENT DOCUMENTS

KR    20210063127 A  *  6/2021

OTHER PUBLICATIONS

Rishi, High-Throughput Technologies for Genome Interrogation and Editing, Thesis, Univ. of California, Berkley, 2019. (Year: 2019).*
Gao et al., Programmable biomolecular switches for rewiring flux in *Escherichia coli*, Nature Comm. 2019, 10:3751. (Year: 2019).*

* cited by examiner

*Primary Examiner* — Todd M Epstein
(74) *Attorney, Agent, or Firm* — SZDC Law PC (57) ABSTRACT

The present invention relates to a recombinant strain for producing shikimic acid, in which a target gene that regulates the asymmetric cell division and target genes that regulate the shikimic acid production are expressed The target gene that regulates the asymmetric cell division includes cytoskeletal protein PopZ coding gene popZ, and the target genes that regulate the shikimic acid production include DAHP synthase coding gene aroG, 3-dehydroquinate synthase coding gene aroB, and transketolase coding gene tktA. The recombinant strain of the present invention realizes the de novo synthesis of shikimic acid using glucose as a substrate, with a low cost. After fermentation with the strain in a 7.5 L fermentor, the highest production of shikimic acid is 88.1 g/L, the yield is 0.33 g/g, and the production intensity of shikimic acid is 1.1 g/L/h.

8 Claims, 3 Drawing Sheets

Specification includes a Sequence Listing.

SEQUENCE LISTING

<160> NUMBER OF SEQ ID NOS: 7

<210> SEQ ID NO 1
<211> LENGTH: 534
<212> TYPE: DNA
<213> ORGANISM: Articifical sequence
<220> FEATURE:
<223> OTHER INFORMATION: Cytoskeletal protein PopZ coding gene popZ

<400> SEQUENCE: 1

```
atgagcgatc agagccagga accgaccatg gaagaaattc tggcgagcat tcgccgcatt      60
atttccgagg acgacgctcc tgccgagccc gcagcagagg ctgctcctcc cccaccccca     120
```

```
gaaccagaac cggaaccggt gagctttgat gatgaagtgc tggaactgac cgatccgatt    180
gcaccagagc ctgagctacc accgctggaa accgtgggcg atattgatgt gtatagtcca    240
cctgagcccg aatcggaacc cgcttacaca cctccaccag cggcgccggt gtttgatcgc    300
gatgaggtag ctgagcaact tgtcggtgta tccgccgcga gcgcagcggc gtcagcgttc    360
ggaagcctga gcagcgcgct gctgatgccg aaagatggcc gcaccctgga agatgtggtg    420
cgcgaactgc tgcgcccgct gctgaaagaa tggctggatc agaacctgcc gcgcattgtg    480
gaaaccaaag tggaagaaga agtgcagcgc attagccgcg ccgcggcgc gtaa            534
```

<210> SEQ ID NO 2
<211> LENGTH: 1053
<212> TYPE: DNA
<213> ORGANISM: Articifical sequence
<220> FEATURE:
<223> OTHER INFORMATION: DAHP synthase coding gene aroG

<400> SEQUENCE: 2

```
atgaattatc agaacgacga tttacgcatc aaagaaatca agagttact tcctcctgtc     60 gcattgctgg aaaaattccc cgctactgaa atgccgcga atacggttgc ccatgcccga    120
aaagcgatcc ataagatcct gaaaggtaat gatgatcgcc tgttggttgt gattggccca    180
tgctcaattc atgatcctgt cgcggcaaaa gagtatgcca ctcgcttgct ggcgctgcgt    240
gaagagctga agatgagct ggaaatcgta atgcgcgtct attttgaaaa gccgcgtacc    300
acggtgggct ggaaagggct gattaacgat ccgcatatgg ataatagctt ccagatcaac    360
gacggtctgc gtatagcccg taaattgctg cttgatatta cgacagcgg tctgccagcg    420 gcaggtgagt ttctcaatat gatcacccca caatatctcg ctgacctgat gagctggggc    480
gcaattggcg cacgtaccac cgaatcgcag gtgcaccgcg aactggcatc agggctttct    540
tgtccggtcg gcttcaaaaa tggcaccgac ggtacgatta agtggctat cgatgccatt    600 aatgccgccg gtgcgccgca ctgcttcctg tccgtaacga aatgggggca ttcggcgatt    660 gtgaataccca gcgtaacgg cgattgccat atcattctgc gcggcggtaa agagcctaac    720
tacagcgcga agcacgttgc tgaagtgaaa gaagggctga caaagcagg cctgccagca    780 caggtgatga tcgatttcag ccatgctaac tcgtccaaac aattcaaaaa gcagatggat    840
gtttgtgctg acgtttgcca gcagattgcc ggtggcgaaa aggccattat tggcgtgatg    900
gtggaaagcc atctggtgga aggcaatcag agcctcgaga gcgggggagcc gctggcctac    960 ggtaagagca tcaccgatgc ctgcatcggc tgggaagata ccgatgctct gttacgtcaa   1020
ctggcgaatg cagtaaaagc gcgtcgcggg taa                                1053
```

<210> SEQ ID NO 3
<211> LENGTH: 1089
<212> TYPE: DNA
<213> ORGANISM: Articifical sequence
<220> FEATURE:
<223> OTHER INFORMATION: 3-Dehydroquinate synthase coding gene aroB

<400> SEQUENCE: 3

```
atggagcgta ttgtcgttac tctcggggaa cgtagttacc caattaccat cgcatctggt     60
ttgtttaatg aaccagcttc attcttaccg ctgaaatcgg gcgagcaggt catgttggtc    120
accaacgaaa ccctggctcc tctgtatctc gataaggtcc gcggcgtact tgaacaggcg    180
ggtgttaacg tcgatagcgt tatcctccct gacggcgagc agtataaaag cctggctgta    240
```

```
ctcgataccg tctttacggc gttgttacaa aaaccgcatg gtcgcgatac tacgctggtg    300
gcgcttggcg gcggcgtagt gggcgatctg accggcttcg cggcggcgag ttatcagcgc    360
ggtgtccgtt tcattcaagt cccgacgacg ttactgtcgc aggtcgattc ctccgttggc    420
ggcaaaactg cggtcaacca tcccctcggt aaaaacatga ttggcgcgtt ctaccaacct    480
gcttcagtgg tggtggatct cgactgtctg aaaacgcttc ccccgcgtga gttagcgtcg    540
gggctggcag aagtcatcaa atacggcatt attcttgacg gtgcgttttt taactggctg    600
gaagagaatc tggatgcgtt gttgcgtctg gacggtccgg caatggcgta ctgtattcgc    660
cgttgttgtg aactgaaggc agaagttgtc gccgccgacg agcgcgaaac cgggttacgt    720
gctttactga atctgggaca cacctttggt catgccattg aagctgaaat ggggtatggc    780
aattggttac atggtgaagc ggtcgctgcg ggtatggtga tggcggcgcg gacgtcggaa    840
cgtctcgggc agtttagttc tgccgaaacg cagcgtatta taaccctgct caagcgggct    900
gggttaccgg tcaatgggcc gcgcgaaatg tccgcgcagg cgtatttacc gcatatgctg    960
cgtgacaaga aagtccttgc gggagagatg cgcttaattc ttccgttggc aattggtaag   1020
agtgaagttc gcagcggcgt ttcgcacgag cttgttctta acgccattgc cgattgtcaa   1080
tcagcgtaa                                                          1089

<210> SEQ ID NO 4
<211> LENGTH: 1992
<212> TYPE: DNA
<213> ORGANISM: Articifical sequence
<220> FEATURE:
<223> OTHER INFORMATION: Transketolase coding gene tktA

<400> SEQUENCE: 4
atgtcctcac gtaaagagct tgccaatgct attcgtgcgc tgagcatgga cgcagtacag     60
aaagccaaat ccggtcaccc gggtgcccct atgggtatgg ctgacattgc cgaagtcctg    120
tggcgtgatt tcctgaaaca caacccgcag aatccgtcct gggctgaccg tgaccgcttc    180
gtgctgtcca acggccacgg ctccatgctg atctacagcc tgctgcacct caccggttac    240
gatctgccga tggaagaact gaaaaacttc cgtcagctgc actctaaaac tccgggtcac    300
ccggaagtgg gttacaccgc tggtgtggaa accaccaccg gtccgctggg tcagggtatt    360
gccaacgcag tcggtatggc gattgcagaa aaaacgctgg cggcgcagtt taaccgtccg    420
ggccacgaca ttgtcgacca ctacacctac gccttcatgg gcgacggctg catgatggaa    480
ggcatctccc acgaagtttg ctctctggcg gtacgctga gctgggtaa actgattgca    540
ttctacgatg acaacggtat ttctatcgat ggtcacgttg aaggctggtt caccgacgac    600
accgcaatgc gtttcgaagc ttacggctgg cacgttattc gcgacatcga cggtcatgac    660
gcggcatcta tcaaacgcgc agtagaagaa gcgcgcgcag tgactgacaa accttccctg    720
ctgatgtgca aaaccatcat cggttttcggt tccccgaaca agccggtac ccacgactcc    780
cacggtgcgc gctgggcga cgctgaaatt gccctgaccc gcaacaact gggctggaaa    840
tatgcgccgt tcgaaatccc gtctgaaatc tatgctcagt gggatgcgaa agaagcaggc    900
caggcgaaag aatccgcatg gaacgagaaa ttcgctgctt acgcgaaagc ttatccgcag    960
gaagccgctg aatttacccg ccgtatgaaa ggcgaaatgc cgtctgactt cgacgctaaa   1020
gcgaaagagt tcatcgctaa actgcaggct aatccggcga aaatcgccag ccgtaaagcg   1080
tctcagaatg ctatcgaagc gttcggtccg ctgttgccgg aattcctcgg cggttctgct   1140
gacctggcgc cgtctaacct gaccctgtgg tctggttcta agcaatcaa cgaagatgct   1200
```

-continued

| | |
|---|---|
| gcgggtaact acatccacta cggtgttcgc gagttcggta tgaccgcgat tgctaacggt | 1260 |
| atctccctgc acggtggctt cctgccgtac acctccacct tcctgatgtt cgtggaatac | 1320 |
| gcacgtaacg ccgtacgtat ggctgcgctg atgaaacagc gtcaggtgat ggtttacacc | 1380 |
| cacgactcca tcggtctggg cgaagacggc ccgactcacc agccggttga gcaggtcgct | 1440 |
| tctctgcgcg taaccccgaa catgtctaca tggcgtccgt gtgaccaggt tgaatccgcg | 1500 |
| gtcgcgtgga aatacggtgt tgagcgtcag gacggcccga ccgcactgat cctctcccgt | 1560 |
| cagaacctgg cgcagcagga acgaactgaa gagcaactgg caaacatcgc gcgcggtggt | 1620 |
| tatgtgctga agactgcgc cggtcagccg gaactgattt tcatcgctac cggttcagaa | 1680 |
| gttgaactgg ctgttgctgc ctacgaaaaa ctgactgccg aaggcgtgaa agcgcgcgtg | 1740 |
| gtgtccatgc cgtctaccga cgcatttgac aagcaggatg ctgcttaccg tgaatccgta | 1800 |
| ctgccgaaag cggttactgc acgcgttgct gtagaagcgg gtattgctga ctactggtac | 1860 |
| aagtatgttg gcctgaacgg tgctatcgtc ggtatgacca ccttcggtga atctgctccg | 1920 |
| gcagagctgc tgtttgaaga gttcggcttc actgttgata cgttgttgc gaaagcaaaa | 1980 |
| gaactgctgt aa | 1992 |

<210> SEQ ID NO 5
<211> LENGTH: 720
<212> TYPE: DNA
<213> ORGANISM: Articifical sequence
<220> FEATURE:
<223> OTHER INFORMATION: Green fluorescent protein gfp gene

<400> SEQUENCE: 5

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagtaa | 720 |

<210> SEQ ID NO 6
<211> LENGTH: 1152
<212> TYPE: DNA
<213> ORGANISM: Articifical sequence
<220> FEATURE:
<223> OTHER INFORMATION: Alcohol dehydrogenase

<400> SEQUENCE: 6

| | |
|---|---|
| atggcatctt caactttctt tattccttct gtgaatgtca tcggcgctga ttcattgact | 60 |
| gatgcaatga atatgatggc agattatgga tttacccgta ccttaattgt cactgacaat | 120 |
| atgttaacga aattaggtat ggcgggtgat gtgcaaaaag cactggaaga acgcaatatt | 180 |

| | |
|---|---|
| tttagcgtta tttatgatgg cacccaacct aacccaacca cggaaaacgt cgccgcaggt | 240 |
| ttgaaattac ttaaagaaaa taattgcgat agcgtgattt ccttaggcgg tggttctccg | 300 |
| catgactgtg caaaaggtat tgcgctggtg gcagccaatg gtggtgatat ccgtgattat | 360 |
| gaaggcgttg accgctctgc aaaaccgcag ctgccgatga tcgccatcaa taccactgcg | 420 |
| ggtacagcat cagaaatgac tcgtttctgc atcatcaccg acgaagcgcg tcacatcaaa | 480 |
| atggcgattt tgataagca cgtgactccg ctgctttctg tcaatgactc ctcgctgatg | 540 |
| atcggtatgc cgaagtcact gaccgccgcc actggtatgg acgccttaac gcacgctatc | 600 |
| gaagcgtatg tttctattgc cgccacgccg atcactgacg cttgtgcact gaaagccgtg | 660 |
| accatgattg ccgaaaacct gccgttagcc gttgaagatg gcagtaatgc gaaagcgcgt | 720 |
| gaagcaatgg cttatgccca gttcctcgcc ggtatggcgt tcaataatgc ttctctgggt | 780 |
| tatgttcatg cgatggcgca ccagctgggc ggtttctaca acctgccaca cggtgtatgt | 840 |
| aacgccgttt tgctgccgca tgttcaggta ttcaacagca agtcgccgc cgcacgtctg | 900 |
| cgtgactgtg ccgctgcaat gggcgtgaac gtgacaggta aaaacgatgc ggaaggtgct | 960 |
| gaagcctgca ttaacgccat ccgtgaactg gcgaagaaag tggatatccc ggcaggccta | 1020 |
| cgcgacctga acgtgaaaga agaagatttc gcggttctgg cgactaatgc cctgaaagat | 1080 |
| gcctgtggtt ttactaaccc gatccaggca actcacgaag aaattgtggc gatttatcgc | 1140 |
| gcagcgatgt aa | 1152 |

<210> SEQ ID NO 7
<211> LENGTH: 1203
<212> TYPE: DNA
<213> ORGANISM: Articifical sequence
<220> FEATURE:
<223> OTHER INFORMATION: Acetate kinase

<400> SEQUENCE: 7

| | |
|---|---|
| atgtcgagta agttagtact ggttctgaac tgcggtagtt cttcactgaa atttgccatc | 60 |
| atcgatgcag taaatggtga agagtacctt tctggtttag ccgaatgttt ccacctgccc | 120 |
| gaagcacgta tcaaatggaa aatggacggc aataaacagg aagcggcttt aggtgcaggc | 180 |
| gccgctcaca gcgaagcgct caactttatc gttaatacta ttctggcaca aaaaccagaa | 240 |
| ctgtctgcgc agctgactgc tatcggtcac cgtatcgtac acggcggcga aaagtatacc | 300 |
| agctccgtag tgatcgatga gtctgttatt cagggtatca agatgcagc ttcttttgca | 360 |
| ccgctgcaca acccggctca cctgatcggt atcgaagaag ctctgaaatc tttcccacag | 420 |
| ctgaaagaca aaaacgttgc tgtatttgac accgcgttcc accagactat gccggaagag | 480 |
| tcttacctct acgccctgcc ttacaacctg tacaaagagc acggcatccg tcgttacggc | 540 |
| gcgcacggca ccagccactt ctatgtaacc caggaagcgg caaaaatgct gaacaaaccg | 600 |
| gtagaagaac tgaacatcat cacctgccac ctgggcaacg gtggttccgt ttctgctatc | 660 |
| cgcaacggta aatgcgttga cacctctatg ggcctgaccc cgctggaagg tctggtcatg | 720 |
| ggtacccgtt ctggtgatat cgatccggcg atcatcttcc acctgcacga caccctgggc | 780 |
| atgagcgttg acgcaatcaa caaactgctg accaaagagt ctggcctgct gggtctgacc | 840 |
| gaagtgacca gcgactgccg ctatgttgaa gacaactacg cgacgaaaga agacgcgaag | 900 |
| cgcgcaatgg acgtttactg ccaccgcctg gcgaaataca tcggtgccta cactgcgctg | 960 |
| atggatggtc gtctggacgc tgttgtattc actggtggta tcggtgaaaa tgccgcaatg | 1020 |
| gttcgtgaac tgtctctggg caaactgggc gtgctgggct ttgaagttga tcatgaacgc | 1080 |

-continued

```
aacctggctg cacgtttcgg caaatctggt ttcatcaaca aagaaggtac ccgtcctgcg  1140
gtggttatcc caaccaacga agaactggtt atcgcgcaag acgcgagccg cctgactgcc  1200
tga                                                                1203
```

RECOMBINANT STRAIN FOR PRODUCING SHIKIMIC ACID, AND CONSTRUCTION METHOD AND USE THEREOF

This application is a Continuation-in-part Application of PCT/CN2021/135282, filed on Dec. 3, 2021, which claims priority to Chinese Patent Application No. 202111425348.1, filed on Nov. 26, 2021, which is incorporated by reference for all purposes as if fully set forth herein.

FIELD OF THE INVENTION

The present invention relates to the technical field of biological engineering, and more particularly to a recombinant strain producing shikimic acid, and a construction method and use thereof.

DESCRIPTION OF THE RELATED ART

Shikimic acid is a good pharmaceutical intermediate that inhibits the platelet aggregation and inhibits the arterial, venous and cerebral thrombosis by affecting the metabolism of arachidonic acid. It also has anti-inflammatory and analgesic effects, and can also be used as anti-viral, anti-thrombotic, anti-ischemic and anti-cancer drugs. Shikimic acid is also an important microbial metabolite and a raw material for the synthesis of alkaloids, aromatic amino acids and indole derivatives, and has extremely high application value. In recent years, as a precursor for synthesizing Tamiflu, the only effective drug against avian influenza, shikimic acid has attracted much attention.

The shikimate pathway is widely present in plants, and microorganisms such as bacteria, and the use of microbial engineering bacteria to synthesize shikimic acid has significant advantages in terms of production scale, production technology and production period, thus becoming a research hotspot in many pharmaceutical companies and laboratories in China and other countries. The shikimate pathway is a process in which phosphoenolpyruvate and erythrose-4-phosphate are used as the starting substrates, shikimic acid is produced after a series of conversions in the presence of catalytic enzymes in an organism, and then a series of aromatic compounds are synthesized with shikimic acid as an intermediate compound, such as tyrosine, phenylalanine, and tryptophan. In biological cells, glucose as an initial substrate is available to synthesize phosphoenolpyruvate by the glycolysis pathway and to synthesize erythrose-4-phosphate by the pentose phosphate pathway. In the shikimate pathway in an organism, phosphoenolpyruvate and erythrose-4-phosphate as starting compounds are condensed to form 3-deoxy-D-arabinoheptulosonate-7-phosphate in the presence of 3-deoxy-D-arabinoheptulosonate-7-phosphate (DAHP) synthase, then, DAHP is catalyzed by 3-dehydroquinate (DHQ) synthase to produce 3-dehydroquinate, DHQ is then converted into 3-dehydroshikimic acid (DHS) in the presence of 3-dehydroquinate dehydratase, and DHS is converted into shikimic acid (SA) in the presence of shikimate dehydratase. Shikimic acid is catalyzed by shikimate kinase to produce shikimate 3-phosphate (abbreviated as S3P). Subsequently, in the presence of a series of enzymes, shikimate 3-phosphate is respectively converted into aromatic amino acids such as phenylalanine, tyrosine, and tryptophan by chorismate (CHA).

The current methods for producing shikimic acid mainly include control of the expression level of enzymes in the pathway, regulation of the supply of cofactors, optimization of the starting strains and the fermentation conditions. For example, (i) a path-independent dynamic control system based on quorum sensing is designed to separate the cell growth and shikimic acid production, and achieve the effective accumulation of shikimic acid of 105 mg/L. (ii) Regulation of degradation by protease is combined with the growth-phase promoter and the stationary-phase promoter to separate the cell growth and shikimic acid production, and produce shikimic acid in an amount of 12.63 g/L. (iii) The highest shikimic acid production (141 g/L) is obtained in *Corynebacterium glutamicum* using the growth-arrested response of cells. However, there are problems such as low content, difficult downstream separation, long time-consuming, and high contamination. Therefore, there is still a need to find a new method of producing shikimic acid.

SUMMARY OF THE INVENTION

To solve the above technical problems, the present invention provides a strategy for regulating asymmetric cell division to improve the production of shikimic acid. A cytoskeletal protein is used to regulate asymmetric cell division, and regulate different cell functions. By introducing asymmetrical division of targeted cells, the cell growth is separated from shikimic acid production to allow more shikimic acid to be accumulated.

A first object of the present invention is to provide a recombinant strain producing shikimic acid, in which a target gene that regulates asymmetric cell division and target genes that regulate shikimic acid production are expressed. The target gene that regulates asymmetric cell division includes cytoskeletal protein PopZ coding gene popZ, and the target genes that regulate shikimic acid production include DAHP synthase coding gene aroG, 3-dehydroquinate synthase coding gene aroB, and transketolase coding gene tktA. In the present invention, the order of gene expression is aroB, aroG and tktA, and shikimate kinase I and II (aroK and aroL genes) are both knocked out.

Preferably, the recombinant strain is constructed with the *E. coli* strain GL0002 as a host. The strain GL0002 (for producing lactic acid) is described in Guo L, Zhang F, Zhang C, Hu G, Gao C, Chen X, et al. Enhancement of malate production through engineering of the periplasmic rTCA pathway in *Escherichia coli*. Biotechnol Bioeng 2018, 115 (6):1571-1580 (hereafter "Guo Reference"). The Guo Reference is incorporated by reference. The strain GL0002 was deposited at China Center for Type Culture Collection on Jun. 4, 2025 under CCTCC Deposit Number: CCTCC NO: M 20251260. The *E. coli* GL0002 is obtained by knocking out the gene coding alcohol dehydrogenase (adhE, SEQ ID NO:6) and the gene coding acetate kinase (ackA, SEQ ID NO:7) from the starting strain *E. coli* ATCC 8739.

Preferably, the recombinant strain is constructed using pETac-PopZ and PJ01-GAB as expression vectors. The expression vector pETac-PopZ is constructed by ligating the gene popZ to the vector pETac, and the expression vector PJ01-GAB is constructed by ligating the gene aroB, the gene aroG, and the gene tktA sequentially to the vector PJ01.

Preferably, the expression vector is obtained by inserting a gene fragment containing B0034RBS into the vector by homologous recombination. For example, the expression vector PJ01-GAB is obtained by sequentially inserting the aroB gene containing B0034RBS, the aroG gene containing B0034RBS, and the tktA gene containing B0034RBS into the vector PJ01 by homologous recombination.

Preferably, the cytoskeletal protein PopZ coding gene popZ has a nucleotide sequence as shown in SEQ ID NO: 1.

Preferably, the DAHP synthase coding gene aroG has a nucleotide sequence as shown in SEQ ID NO: 2.

Preferably, the 3-dehydroquinate synthase coding gene aroB has a nucleotide sequence as shown in SEQ ID NO: 3.

Preferably, the transketolase coding gene tktA has a nucleotide sequence as shown in SEQ ID NO: 4.

Preferably, the expression mode of the target gene that regulates the asymmetric cell division and the target genes that regulate the shikimic acid production is free expression.

A second object of the present invention is to provide a method for constructing the recombinant strain, which comprises the following steps:

inserting the popZ fragment into the plasmid pETac, to obtain a recombinant plasmid pETac-PopZ; sequentially ligating the aroB, aroG, and tktA fragments in tandem to the plasmid PJ01 to construct a recombinant plasmid PJ01-GAB; and transforming the recombinant plasmid pETac-PopZ and the recombinant plasmid PJ01-GAB into the strain GL0002 to obtain a recombinant strain.

Specifically, the recombinant plasmid PJ01-GAB is constructed through a process as follows.

(1) Based on the commercial plasmid pTargetF (Addgene Plasmid #62226), the T7Te terminator sequence is inserted after the rrnB T1 terminator by whole plasmid PCR to reduce the leaky expression. Further, the sgRNA expression framework is removed by whole plasmid PCR to obtain the engineering plasmid pJ01 containing only the Pj23119 constitutive promoter and two terminators.

(2) Using the genome of E. coli as a template, the aroB$^{opt}$, aroG$^{fbr}$, and tktA fragments containing B0034RBS are amplified respectively. The aroB$^{opt}$ fragment is inserted into the expression framework of PJ01 by multi-fragment one-step homologous recombination to obtain the plasmid PJ01-B. Following the same method, the aroG$^{fbr}$ and tktA fragments are inserted into the expression framework of PJ01 by multi-fragment one-step homologous recombination to obtain the plasmid PJ01-GAB.

Specifically, the recombinant plasmid pETac-PopZ is constructed through a process as follows.

Using the genome of Escherichia coli MG1655 as a template, primers containing B0034RBS are designed, with which the popZ gene containing B0034RBS derived from Caulobacter crescentus is amplified. The product is inserted into the plasmid pETac digested with BamH1 by homologous recombination to obtain the plasmid pETac-PopZ.

A third object of the present invention is to provide a method for producing shikimic acid, which includes producing shikimic acid by fermentation using the recombinant strain.

Preferably, the fermentation medium includes NBS inorganic salt medium.

Preferably, the fermentation conditions include a temperature of 35-38° C., a revolving speed of 200-220 rpm, an initial $OD_{600}$ of 0.04-0.1 for fermentation, and fermentation time of 70-90 h, for example, 75 h; or a temperature of 35-38° C., a revolving speed of 480-530 rpm, an inoculation amount of 5-10%, a liquid load of 30-50%, a pH of 6.0-7.0, an initial $OD_{600}$ of 0.04-0.3 for fermentation, an air flow rate of 1-2 vvm, and fermentation time of 72-100 h, and 80 h in one embodiment of the present invention.

The recombinant strain can be used to produce proteins, for example, the protein expressed by the target gene that regulates asymmetric cell division, the proteins expressed by the target genes that regulate shikimic acid production, and fusion proteins; and can be used to produce shikimic acid and products containing shikimic acid.

By virtue of the above solutions, the present invention has the following advantages.

The recombinant strain constructed in the present invention expresses the target gene that regulates the asymmetric cell division and the target genes that regulate the shikimic acid production, and can realize the de novo synthesis of and conversion into shikimic acid by microbial method using glucose as a substrate, with a low cost. The production, yield and production intensity of shikimic acid reach 88.1 g/L, 0.33 g/g, and 1.1 g/L/h respectively. The production of shikimic acid is the highest among the productions of shikimic acid produced by Escherichia coli, and is about 5% higher than the currently reported production.

The above description is only a summary of the technical solutions of the present invention. To make the technical means of the present invention clearer and implementable in accordance with the disclosure of the specification, the preferred embodiments of the present invention will be described in detail with reference to the accompanying drawings.

BRIEF DESCRIPTION OF THE DRAWINGS

To make the disclosure of the present invention more comprehensible, the present invention will be further described in detail by way of specific embodiments of the present invention with reference the accompanying drawings, in which.

DETAILED DESCRIPTION OF THE PREFERRED EMBODIMENTS

The present invention will be further described below with reference to the accompanying drawings and specific examples, so that those skilled in the art can better understand and implement the present invention; however, the present invention is not limited thereto.

Materials and methods involved in the examples:

The plasmid is constructed by a typical molecular biology method.

The cell morphological parameters are measured using a fluorescence microscope (Nikon microscop, 80i) at an ambient temperature controlled to 30° C.

Seed medium: LB medium, containing peptone 10 g/L, yeast powder 5 g/L, and sodium chloride 10 g/L.

Fermentation medium: including a standard fermentation medium (NBS medium, 1 L), $K_2HPO_4$ (7.5 g), ferric ammonium (III) citrate (0.3 g), citric acid monohydrate (2.1 g), L-phenylalanine (0.7 g), L-tyrosine (0.7 g), L-Tryptophan (0.35 g), and concentrated $H_2SO_4$ (1.2 mL). The fermentation medium is adjusted to pH 7.0 by adding concentrated aqueous ammonia before reaching a high pressure. The following supplements are added immediately before fermentation: glucose, $MgSO_4$ (0.24 g), p-hydroxybenzoic acid (0.010 g), potassium p-aminobenzoate (0.010 g), 2,3-dihydroxybenzoic acid (0.010 g) and trace minerals $(NH_4)_6(Mo_7O_{24})\cdot 4H_2O$ (0.0037 g), $ZnSO_4\cdot 7H_2O$ (0.0029 g), $H_3BO_3$ (0.0247 g), $CuSO_4\cdot 5H_2O$ (0.0025 g), and $MnCl_2\cdot 4H_2O$ (0.0158 g), and methyl-α-d-glucopyranoside of a final concentration of 1 mM. The glucose, MgSO$_4$, and methyl-α-d-glucopyranoside solutions are respectively autoclaved, and the aromatic vitamin and trace mineral solutions are sterilized with a 0.22 μM membrane. Before adding the fermentation medium, pH is adjusted to 7 with KOH, and the system is sterilized with a 0.22 μm membrane. An antifoaming agent (Sigma 204) is added as needed.

Preparation of fermentation sample: A fermentation broth sample is centrifuged at 12000 rpm for 5 min, the supernatant is collected, diluted, and filtered through a 0.22 μm aqueous-system filter membrane. The filtrate is analyzed by liquid chromatography analysis.

Determination of polylactic acid content: Dionex High Performance Liquid Chromatograph (with UV-Vis detector), Bio-Rad Aminex HPX-87H (300×7.8 mm, 9 μm) chromatographic column; mobile phase: 0.005 M H$_2$SO$_4$ filtered through 0.22 μm filter and ultrasonically degassed; flow rate: 0.6 mL/min; column temperature: 35° C.; and UV detection wavelength: 210 nm.

Example 1: Screening of Asymmetric Division Gene

The popZ gene encoding asymmetric cell division and the green fluorescent protein gfp gene (having a nucleotide sequence as shown in SEQ ID NO: 5) were fused, to obtain the GFP-PopZ protein. B0034RBS was inserted at the upstream ATG position of the fused gene by fusion PCR. The PCR product was recovered, and ligated, by homologous recombination, to the vector pETac plasmid digested at BamH1 and Sall restriction sites, to obtain the recombinant plasmid pETac-GFP-PopZ. The pETac-GFP plasmid was constructed similarly.

The obtained recombinant plasmids pETac-GFP-PopZ and pETac-GFP were introduced into competent cells *E. coli* JM109, respectively. Strains carrying the asymmetric cell division gene pETac-GFP-PopZ and the pETac-GFP plasmid were obtained, respectively.

Figure 1:
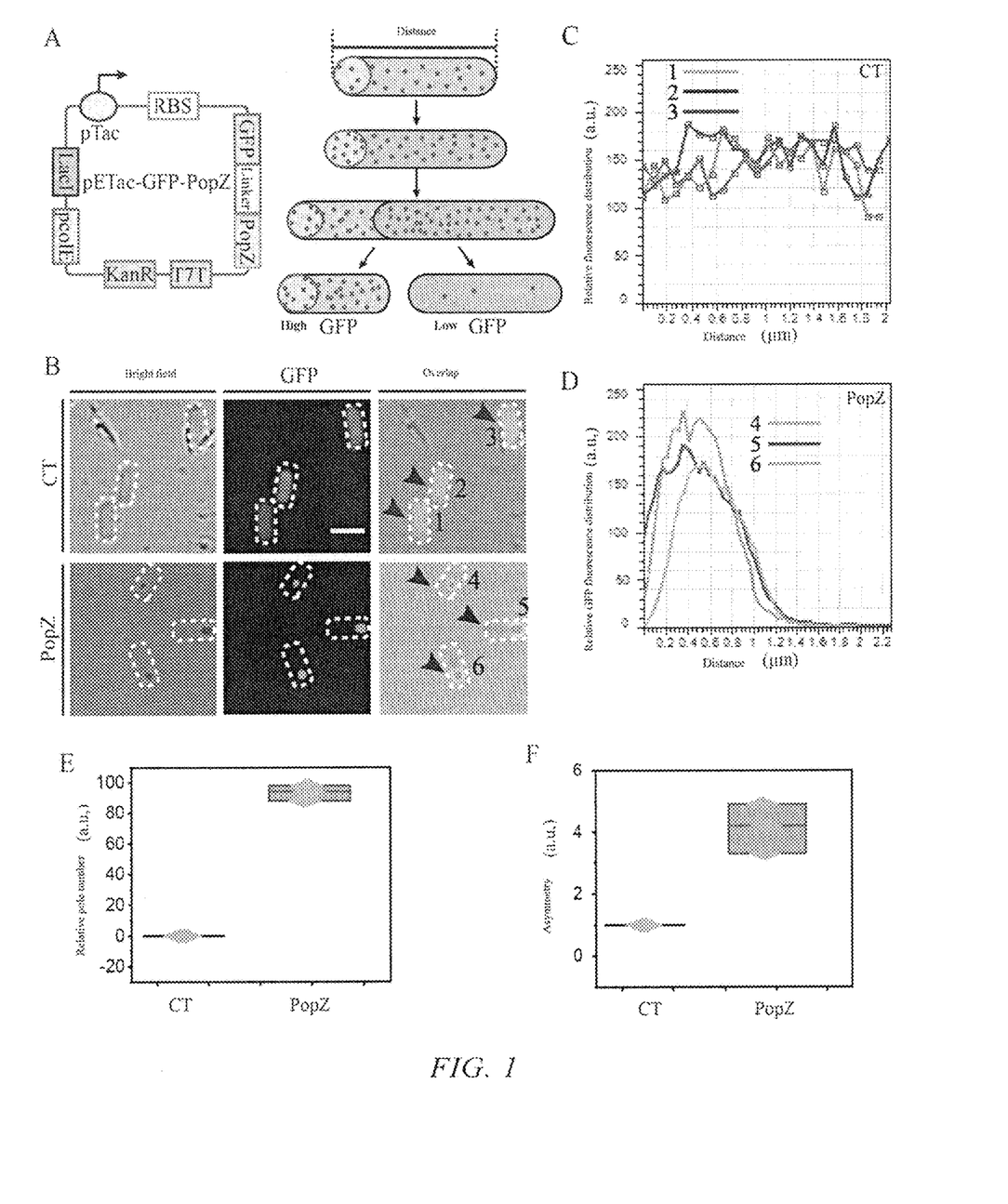
FIG. 1 shows the regulation of parameters in asymmetric cell division.

In LB medium, the above strains were evaluated for parameters of asymmetric cell division by fluorescence microscopy. The results are shown in FIG. 1. It can be seen from FIGS. 1A-D, the GFP-PopZ fusion protein is expressed, and this allows GFP to accumulate at a pole of the cells. The data was analyzed by software matching with the fluorescence microscopy. The results show that the relative fluorescence distribution of GFP in the strain expressing GFP-PopZ fusion protein is higher at one end, and the control group shows a uniform GFP fluorescence distribution. Further, the relative pole number (1E) and the asymmetry (1F) of the strain were analyzed. The relative pole number and asymmetry of the strain expressing GFP-PopZ fusion protein reach 92% and 3.8, respectively. The results show that asymmetric cell division can be achieved effectively by expression of PopZ.

Example 2. Production of Shikimic Acid by Shake-Flask Fermentation

Figure 2:
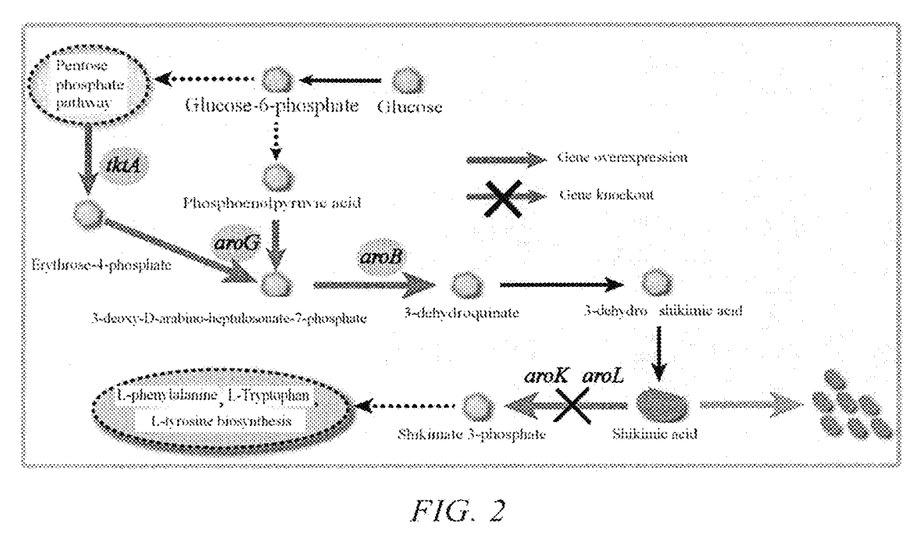
FIG. 2 shows the production path of shikimic acid.

The constructed vectors PJ01-GAB and pETac-PopZ expressing related genes in the shikimic acid synthesis pathway (FIG. 2) were introduced into the competent cells of S1 (strain GL0002), and a recombinant GS strain for producing shikimic acid and carrying PJ01-GAB and pETac-PopZ was obtained. The *E. coli* GL0002 is obtained by knocking out the gene coding alcohol dehydrogenase (adhE, SEQ ID NO:6) and the gene coding acetate kinase (ackA, SEQ ID NO:7) from the starting strain *E. coli* ATCC 8739.

The fermentation conditions for shikimic acid production were: 37° C., 220 rpm, initial OD$_{600}$ of 0.1 for fermentation, and fermentation time of 75 h.

Figure 3:
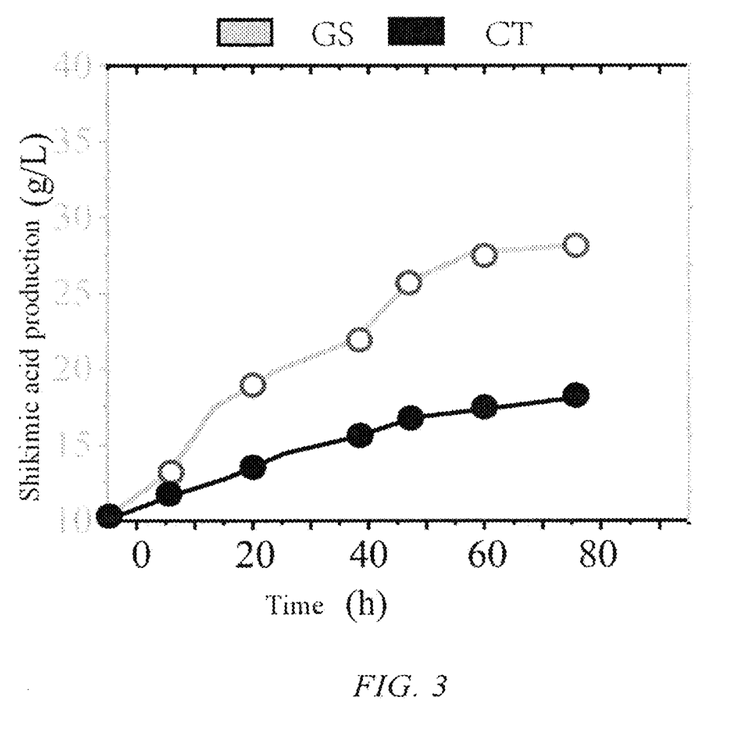
FIG. 3 shows the amount of shikimic acid produced in the control group CT and in the experimental group GS within 75 h of shake flask fermentation.

The shikimic acid-producing strain was cultured in NBS medium, and the content was determined. The results are shown in FIG. 3. With the extension of the bacterial culture time, the shikimic acid content in the control group CT is increased to 18.2 g/L, and the yield reaches 0.29 g/g. The shikimic acid content of the GS strain in the experimental group is increased to 28.2 g/L, and the yield reaches 0.33 g/g, which are respectively 54.9% and 13.8% higher than the control group.

Example 3: Production of Shikimic Acid in a Fermentor

The fermentation performance with the GS strain was detected in a 7.5 L fermentor. The fermentation conditions for shikimic acid production were 38° C., 480 rpm, inoculation amount of 5%, liquid load of 46%, pH of 7.0, initial OD$_{600}$ of 0.3 for fermentation, air flow rate of 1 vvm, and fermentation time of 80 h.

Figure 4:
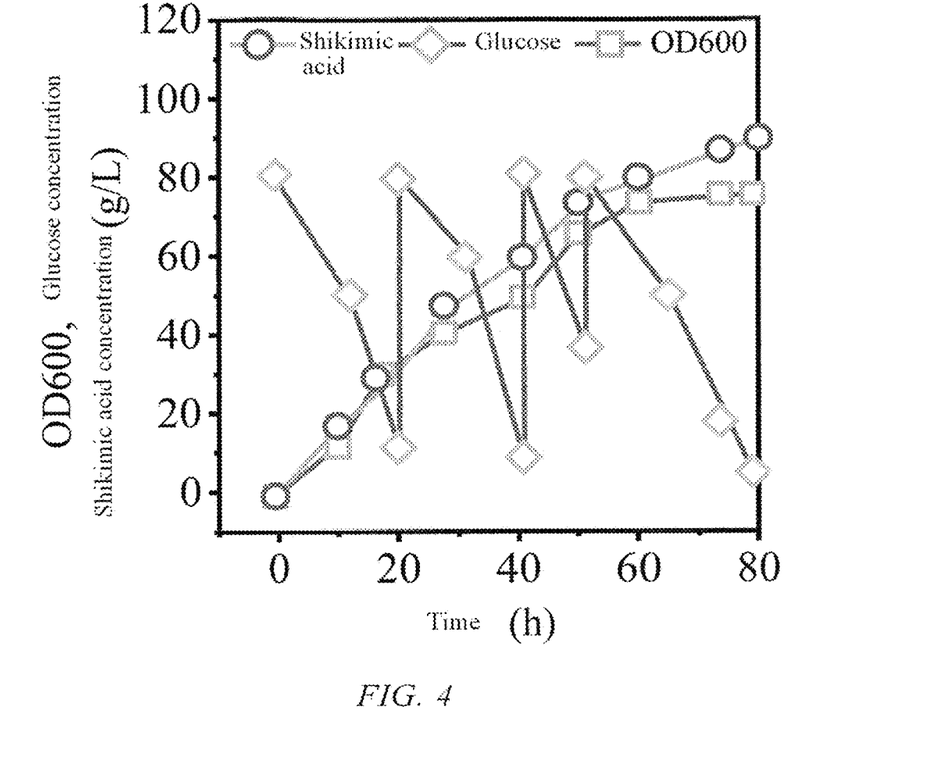
FIG. 4 shows the amount of shikimic acid produced in the fermentor after 80 h of fermentation.

As shown in FIG. 4, at the end of fermentation, the production and yield of shikimic acid reach 88.1 g/L, 0.33 g/g, respectively.

Apparently, the above-described embodiments are merely examples provided for clarity of description, and are not intended to limit the implementations of the present invention. Other variations or changes can be made by those skilled in the art based on the above description. The embodiments are not exhaustive herein. Obvious variations or changes derived therefrom also fall within the protection scope of the present invention.

What is claimed is:

1. A recombinant strain for producing shikimic acid, wherein in the recombinant strain a shikimate kinase I coding gene aroK and a shikimate kinase II coding gene aroL are knocked out, and a target gene that regulates the asymmetric cell division and target genes that regulate the shikimic acid production are expressed, the target gene that regulates the asymmetric cell division comprises a cytoskeletal protein PopZ coding gene popZ, and the target genes that regulate the shikimic acid production are 3-dehydroquinate synthase coding gene aroB, DAHP synthase coding gene aroG, and transketolase coding gene tktA, wherein the recombinant strain is constructed with strain GL0002 as a host and the strain GL0002 was deposited in China Center for Type Culture Collection (Address: Bayi Road, Wuchang District, Wuhan City, Hubei Province) under the Accession No. CCTCC M 20251260 on Jun. 4, 2025.

2. The recombinant strain according to claim 1, wherein the recombinant strain is constructed by using pETac-PopZ and PJ01-GAB as expression vectors, wherein pETac-PopZ is constructed by ligating the gene popZ to a vector pETac, and PJ01-GAB is constructed by ligating the gene aroB, the gene aroG, and the gene tktA sequentially to a vector PJ01.

3. The recombinant strain according to claim 2, wherein the expression vectors are constructed by inserting the gene popZ containing B0034RBS into the vector pETac to obtain pETac-PopZ; and inserting the genes aroB, aroG and tktA containing B0034RBS sequentially into the vector PJ01 to obtain PJ01-GAB.

4. The recombinant strain according to claim 1, wherein the cytoskeletal protein PopZ coding gene popZ has the nucleotide sequence as shown in SEQ ID NO: 1.

5. A method for constructing the recombinant strain according to claim 1, comprising steps of:

inserting a popZ fragment into a plasmid pETac, to obtain a recombinant plasmid pETac-PopZ; sequentially ligating a aroB, aroG, and tktA fragment in tandem to a plasmid PJ01 to construct a recombinant plasmid PJ01-GAB; and transforming the recombinant plasmid pETac-PopZ and the recombinant plasmid PJ01-GAB into a strain GL0002 to obtain the recombinant strain.

6. A method for producing shikimic acid, comprising fermenting a substrate with the recombinant strain according to claim 1 to produce shikimic acid.

7. The method according to claim 6, wherein fermentation conditions comprise a temperature of 35-38° C., a revolving speed of 480-530 rpm, an inoculation amount of 5-10%, a liquid load of 30-50%, a pH of 6.0-7.0, an initial $OD_{600}$ of 0.04-0.3 for fermentation, an air flow rate of 1-2 vvm, and fermentation time of 72-100 h.

8. The method according to claim 6, wherein the fermentation conditions comprise a temperature of 35-38° C., a revolving speed of 200-220 rpm, an initial $OD_{600}$ of 0.04-0.1 for fermentation, and fermentation time of 70-90 h.

* * * * *